United States Patent
Khopade et al.

(10) Patent No.: US 9,629,852 B2
(45) Date of Patent: Apr. 25, 2017

(54) OPHTHALMIC COMPOSITION COMPRISING A PROSTAGLANDIN

(75) Inventors: Ajay Jaysingh Khopade, Baroda (IN); Arindam Halder, Baroda (IN); Subhas Balaram Bhowmick, Baroda (IN)

(73) Assignee: SUN PHARMA ADVANCED RESEARCH COMPANY LTD., Mumbai (IN)

( * ) Notice: Subject to any disclaimer, the term of this patent is extended or adjusted under 35 U.S.C. 154(b) by 332 days.

(21) Appl. No.: 12/601,429

(22) PCT Filed: Oct. 15, 2008

(86) PCT No.: PCT/IN2008/000671
§ 371 (c)(1),
(2), (4) Date: Jan. 21, 2010

(87) PCT Pub. No.: WO2009/084021
PCT Pub. Date: Jul. 9, 2009

(65) Prior Publication Data
US 2010/0137432 A1 Jun. 3, 2010

(30) Foreign Application Priority Data
Oct. 16, 2007 (IN) .......................... 2061/MUM/2007

(51) Int. Cl.
*A61K 31/5575* (2006.01)
*A61K 9/00* (2006.01)
*A61K 9/107* (2006.01)
*A61K 47/14* (2017.01)

(52) U.S. Cl.
CPC ........ *A61K 31/5575* (2013.01); *A61K 9/0048* (2013.01); *A61K 9/1075* (2013.01); *A61K 47/14* (2013.01)

(58) Field of Classification Search
CPC .............. A61K 31/5575; A61K 9/0048; A61K 9/1075; A61K 47/14
See application file for complete search history.

(56) References Cited

U.S. PATENT DOCUMENTS

| 5,849,792 A | 12/1998 | Schneider | |
| 2005/0049311 A1* | 3/2005 | Baker et al. | 514/573 |
| 2006/0100288 A1* | 5/2006 | Bague et al. | 514/642 |
| 2008/0181867 A1* | 7/2008 | Lambert et al. | 424/85.4 |
| 2009/0062381 A1 | 3/2009 | Hirata et al. | |

FOREIGN PATENT DOCUMENTS

| CA | 2645311 A1 | 9/2007 | |
| WO | 00/16744 A1 | 3/2000 | |
| WO | 2006/050836 A2 | 5/2006 | |
| WO | WO2006/050836 | * | 5/2006 |

OTHER PUBLICATIONS

R. Chanamai & D.J. McClements, Prediction of Emulsion Color from Droplet Characteristics: Dilute Monodisperse Oil-in-water Emulsions, 15 Food Hydrocol. 83 (2001).*
Michelle Wong, et al, Sorption of Unoprostone Isopropyl to Packaging Materials, 307 Intl. J Pharmaceut. 163 (2006).*
Wallace Alward, Medical Management of Glaucoma, 339 N Engl. J Med. 1298, 1300 (col. 2, Para.4) (1998).*
Susan Charman, et al, Self-Emulsifying Drug Delivery Systems: Formulation and Biopharmaceutical Evaluation of an Investigational Lipophilic Compound, 9 Pharma. Res. 87 (1992).*
Colin Pouton, Formulation of Self-Emulsifying Drug Delivery Systems, 25 Adv. Drug Del. Rev. 47 (1997).*
Robert Moss & Warren Sunshine, Micellar Catalysis of Ester Hydrolysis. The Influence of Chirality and Head Group Structure in "Simple" Surfactants, 39 J Org. Chem. 1083 (1974).*
BJ Meakin, IK Winterborn & DJG Davies, The Modifying Effects of a Cationic Surfactant on the Rates of Base Catalyzed Hydrolysis of Esters of Different Structures, 23 J Pharm. Pharmac. 25S (1971).*
International Search Report of PCT/IN 2008/000671, date of mailing Sep. 29, 2009.

* cited by examiner

*Primary Examiner* — Sean Basquill
(74) *Attorney, Agent, or Firm* — Sughrue Mion, PLLC

(57) ABSTRACT

The present invention relates to a pharmaceutical composition suitable for ophthalmic use comprising one or more prostaglandin derivatives or salts, a stabilizing amount of polyethylene glycol hydroxystearate and pharmaceutically acceptable vehicle.

5 Claims, No Drawings

OPHTHALMIC COMPOSITION COMPRISING A PROSTAGLANDIN

FIELD OF THE INVENTION

The present invention relates to pharmaceutical composition suitable for ophthalmic use comprising prostaglandin derivatives.

BACKGROUND OF THE INVENTION

Prostaglandin derivatives are one of the known poorly soluble drugs and are administered via ophthalmic route for treating elevated intraocular pressure. One of the prostaglandin derivatives, latanoprost has been approved in the United States of America for the reduction of elevated intraocular pressure in patients with open-angle glaucoma or ocular hypertension, and is commercially available in the United States of America, under the brand name of XALATAN®. XALATAN® Sterile Ophthalmic Solution is a clear, isotonic, sterile, buffered aqueous solution of latanoprost 0.005% (50 μg/ml) with 0.02% benzalkonium chloride and other excipients, and having a pH of approximately 6.7 and an osmolarity of approximately 267 mOsmol/Kg. It is supplied in clear low density polyethylene bottle with a clear low-density polyethylene dropper tip, a turqouise high density polyethylene screw cap and a tamper-evident clear low-density polyethylene overcap. It is recommended for this product that the unopened bottles be stored under refrigeration at a temperature of approximately 2-8° C. and during shipment to the patient, the bottle may be maintained at temperature up to 40° C. for a period not exceeding 8 days. Once the bottle is opened for use, it may be stored at room temperature up to 25° C. for 6 weeks.

Another prostaglandin derivative, which has been approved in the United States of America for the reduction of intraocular pressure in patients with open-angle glaucoma or ocular hypertension is unoprostone isopropyl. It is commercially available under the brand name of RESCULA®. RESCULA® is a sterile, isotonic, buffered aqueous solution of unoprostone isopropyl 0.15%, with 0.015% benzalkonium chloride and other excipients and having a pH of approximately 5.0-6.5 and an osmolality of 235-300 mOsmol/kg. It is supplied in clear, natural polypropylene bottle with a natural polypropylene dropper tip, a turquoise polypropylene closure and a clear tamper-evident shrink band. The recommended storage temperature for the product is between 2° C. to 25° C.

A pharmaceutical composition suitable for ophthalmic use is generally filled in small volume containers made up of plastics such as polypropylene and polyethylene rather than rigid materials like glass. Glass is not suitable for making containers for ophthalmic use because it is generally not able to meet requirement of dispensing ophthalmic preparations in very small volumes, for example drops.

The prostaglandin derivatives are known to be unstable either because of absorption or adsorption or degradation, when stored in polyethylene containers. For example, United States patent U.S. Pat. No. 6,235,781 (herein after referred to as '781) shows that when the aqueous composition of prostaglandin is stored in polyethylene containers, percentage drug remaining was about 80% indicating loss of the prostaglandin derivatives. The '781 patent discloses a method of increasing the stability of an aqueous prostaglandin composition comprising a prostaglandin and a pharmaceutically acceptable surfactant wherein the method comprises: packaging the aqueous prostaglandin composition in a polypropylene container, provided that the polypropylene container is not packaged in a bag containing an iron oxide oxygen scavenger.

Another prior art, U.S. patent application No. 20050287325 (hereinafter referred to as '325) discloses that latanoprost is prone to sorption onto the naturally derived plastic containers. The '325 patent application claims a container comprising prostaglandin compositions that exhibit less than 20% sorption of the prostaglandin. The containers are restricted to those made of specific polyolefins, such as DuPont® 20 LDPE, Chevron 5502 HDPE, Atofina 3020 PP, polypropylene homopolymers, low ethylene content (<8%) polypropylenes, and polymers (HDPE, PP) with low content of additives (<5%) and with low flexural modulus (<200 kpsi).

U.S. patent application US20060100288 (herein after referred to as '288) discloses an oil in water type emulsion, which comprises colloid particles having an oily core surrounded by an interfacial film, wherein said interfacial film has an overall positive charge and comprises:

1) 0.001% to 0.1% by weight of a cationic agent,
2) 0 to 1% by weight of a non ionic surfactant, and
3) 0 to 0.5% by weight of an anionic surfactant, with at least one of said ionic surfactant and of said anionic surfactant being present. The patent application discloses the use of polyethylene glycol hydroxystearate as one of the non-ionic surfactant that should be used in combination with a cationic agent.

In an attempt to develop a pharmaceutical composition of prostaglandin or its derivatives which can be effectively stored in natural polyethylene containers without any drug loss, the inventors surprisingly found that when the prostaglandin derivatives were formulated with polyethylene glycol hydroxystearate, the sorption problem was reduced substantially. When small amount of oil was added to this pharmaceutical composition, the sorption of prostaglandin derivatives to the polyethylene containers was further reduced. It was also found that an addition of a very small amount of oil gave a pharmaceutical composition comprising prostaglandin and polyethylene glycol hydroxystearate that is non irritant to the ocular mucosa, with improvement in the sorption problem, i.e, no sorption of prostaglandin derivatives onto the low density polyethylene containers.

OBJECTS OF THE INVENTION

It is an object of the present invention to make clear pharmaceutical compositions suitable for ophthalmic use and containing poorly water soluble drugs like prostaglandin derivatives, for example, latanoprost. It is another object of the present invention to make a stable pharmaceutical composition comprising prostaglandin derivatives.

It is yet another object of the present invention to make a pharmaceutical composition suitable for ophthalmic use comprising latanoprost that shows no sorption to the low density polyethylene containers (LDPE).

It was another object of the invention to make a pharmaceutical composition suitable for ophthalmic use comprising prostaglandin derivatives free of quaternary ammonium derivatives.

It is yet another object of the present invention to make a pharmaceutical composition suitable for ophthalmic use comprising prostaglandin derivatives by using a process that is economical in term of energy and time consumption and is further suitable for large scale up.

It is further object of the invention to provide a pharmaceutical composition suitable for ophthalmic use comprising prostaglandin derivatives that causes no irritation to the ocular mucosa.

It is further object of the invention to provide a pharmaceutical composition suitable for ophthalmic use comprising prostaglandin derivatives that is effective in lowering the intraocular pressure.

It is further object of the invention to provide a pharmaceutical composition suitable for ophthalmic use comprising prostaglandin derivatives wherein the composition upon administration shows reduced ocular pigmentation.

It is further object of the invention to provide a pharmaceutical composition suitable for ophthalmic use comprising prostaglandin derivatives that is stable on storage at room temperature.

It is also the object of the present invention to provide a clear pharmaceutical composition suitable for ophthalmic use, said composition comprising prostaglandin derivatives.

SUMMARY OF THE INVENTION

The present invention provides a pharmaceutical composition suitable for ophthalmic use, said composition comprising
 a) prostaglandin derivatives or pharmaceutically acceptable salts
 b) stabilizing amount of polyethylene glycol hydroxystearate
and a pharmaceutically acceptable vehicle.

The present invention also provides a pharmaceutical composition suitable for ophthalmic use, said composition comprising
 a) prostaglandin derivatives or pharmaceutically acceptable salts
 b) stabilizing amount of polyethylene glycol hydroxystearate
 c) oil
and a pharmaceutically acceptable vehicle.

DETAILED DESCRIPTION OF THE INVENTION

The term 'emulsion' is used to mean a homogenous mixture of two liquid phases which do not normally mix such as oil and water. An 'emulsifier' is a substance which aids the formation of an emulsion. The terms 'emulsifier' and 'surfactant' are used interchangeably herein.

The term 'microemulsion' as used herein means a thermodynamically stable dispersion of two immiscible liquids, stabilized by surfactants; it is typically clear because the dispersed droplets are less than 100 nanometers in diameter.

The term 'self emulsifying' means an emulsion that is formed spontaneously without any external energy supply.

The term 'Percent Transmission' as used herein is defined as follows. When light is allowed to pass through a solution, the percentage of incident light which is transmitted through the solution is referred to as "Percent Transmission". The "percent transmission" generally defines the visible clarity of the composition.

According to one embodiment, the present invention provides a pharmaceutical composition suitable for ophthalmic use, said composition comprising
 a) prostaglandin derivatives or its pharmaceutically acceptable salts;
 b) stabilizing amount of polyethylene glycol hydroxystearate
and a pharmaceutically acceptable vehicle.

According to one embodiment, the present invention provides a pharmaceutical composition suitable for ophthalmic use, said composition comprising
 a) prostaglandin derivatives or its pharmaceutically acceptable salts;
 b) stabilizing amount of polyethylene glycol hydroxystearate
 c) oil;
and a pharmaceutically acceptable vehicle.

According to one embodiment of the present invention, there is provided a pharmaceutical composition suitable for ophthalmic use, said composition comprising
 a) latanoprost or its pharmaceutically acceptable salts
 b) stabilizing amount of polyethylene glycol hydroxystearate
 c) castor oil;
and a pharmaceutically acceptable vehicle.

According to one embodiment of the present invention, there is provided a pharmaceutical composition suitable for ophthalmic use, said composition comprising
 a) travoprost or its pharmaceutically acceptable salts
 b) stabilizing amount of polyethylene glycol hydroxystearate
 c) castor oil;
and a pharmaceutically acceptable vehicle.

According to one embodiment of the present invention, there is provided a pharmaceutical composition suitable for ophthalmic use, said composition comprising
 a) bimatoprost or its pharmaceutically acceptable salts
 b) stabilizing amount of polyethylene glycol hydroxystearate
 c) castor oil;
and a pharmaceutically acceptable vehicle.

The prostaglandins derivatives that may be used in the pharmaceutical composition of the present invention includes, but are not limited to, all pharmaceutically acceptable prostaglandins, their derivatives and analogs, and their pharmaceutically acceptable esters and salts (hereinafter collectively referred to as "prostaglandins" or "PG's"), which are useful for reducing intraocular pressure when applied topically to the eye. Such prostaglandins include the natural compounds, such as for example $PGE_1$, $PGE_2$, $PGE_3$, $PGD_2$, $PGF_{1\alpha}$, $PGF_{2\alpha}$, $PGF_{3\alpha}$, $PGI_2$(prostacyclin), as well as analogs and derivatives of these compounds which are known to have similar biological activities of either greater or lesser potencies. Analogs of the natural prostaglandins include but are not limited to: alkyl substitutions (e.g., 15-methyl or 16,16-dimethyl), which confer enhanced or sustained potency by reducing biological metabolism or alter selectivity of action; saturation (e.g. 13,14-dihydro) or unsaturation (e.g., 2,3-didehydro, 13,14-didehydro), which confer sustained potency by reducing biological metabolism or alter selectivity of action; deletions or replacements (e.g. 11-deoxy, 9-deoxo-9-methylene), which enhance chemical stability and/or selectivity of action; and omega chain modifications (e.g., 18,19,20-trinor-17-phenyl, or 17,18,19,20-tetranor-16-phenoxy), which enhance selectivity of action and reduced biological metabolism. Derivatives of these prostaglandins that may be formulated in the compositions of the present invention include all pharmaceutically acceptable salts and esters, which may be attached to the 1-carboxyl group or any of the hydroxyl groups of the prostaglandin by use of the corresponding alcohol or organic acid reagent, as appropriate. The terms "analogs" and "derivatives" include compounds which exhibit functional and physical responses similar to those of prostaglandins per se.

Prostaglandins are well known in the art. Particular prostaglandins that may be formulated in the compositions of the present invention include for example trimoprostil, rioprostil, cloprostenol, fluprostenol, luprostiol, etiproston, tiaprost, latanoprost, travoprost, bimatoprost, unoprostone and its derivatives like unoprostone isopropyl, misoprostol, sulfoprostone, gemeprost, alfaprostol, delprostenate, and the like. Pharmaceutical compositions of the present invention include one or more prostaglandins as described above in an amount between about 0.00001% w/v and about 0.2% w/v.

In one embodiment of the present invention, latanoprost which is a prostaglandin F2a analogue, namely isopropyl-(Z)-7[(1R,2R,3R,5S)3,5-dihydroxy-2-[(3R)-3-hydroxy-5-phenylpentyl]cyclopentyl]-5-heptenoate is used. It may be present in an amount ranging from about 0.00001% w/v to about 0.2% w/v. Preferably, latanoprost is used in amounts of about 0.005% w/v. In another embodiment, travoprost is used as the prostaglandin derivative in amounts ranging from about 0.00001% w/v to about 0.2% w/v preferably in an amount 0.004% w/v. In yet another embodiment, bimatoprost is used as the prostaglandin derivative in amounts ranging from about 0.00001% w/v to about 0.2% w/v, preferably in an amount 0.03% w/v.

Polyethylene glycol hydroxystearate is a non ionic surfactant having a HLB value in the range of 14.0 to 16.0. The surfactant has polyglycol ester of 12-hydroxystearic acid (70%) as the hydrophobic component and polyethylene glycol (30%) as the hydrophilic component. The main fatty acid component is 12-hydroxystearic acid (12 HSA) with stearic acid and palmitic acid also present in detectable amounts. SOLUTOL® HS 15 is one such polyethylene glycol hydroxystearate manufactured by BASF which is commercially available as a white paste at room temperature.

The term 'stabilizing amount' as used herein means an amount of polyethylene glycol hydroxystearate that substantially reduces or prevents the adsorption of prostaglandin derivatives onto the containers when stored in containers such as those made up of low density polyethylene, during shelf-life of the product. The term 'substantially reduces the sorption' as used herein means that not more than 20% of sorption of prostaglandin to the container; preferably not more than 15% of sorption of prostaglandin to the container, when the composition is stored at recommended temperature during the shelf life of the product. The said stabilizing amount of polyethylene glycol hydroxystearate is found to cause no toxic effect or irritation to the ocular mucosa upon administration for a long time.

The stabilizing amount of polyethylene glycol hydroxystearate according to the present invention ranges from about 0.001% to about 3.0% weight by volume of the composition. In the preferred embodiments of the present invention, the amount of polyethylene glycol hydroxystearate may range from about 0.1% to about 1.0%, preferably 0.2% to about 0.75% weight by volume of the composition. Further incorporation of oil in the composition allows a lesser stabilizing amount of polyethylene glycol hydroxystearate. For example, generally, when castor oil is added to the composition, the ratio of oil to polyethylene glycol hydroxystearate may be less than 1.0.

According to one embodiment of the present invention, oil may be used in compositions. The oil used may be any oil derived from vegetable, animal or mineral source and/or mixtures thereof. Examples of oils that may be used in the pharmaceutical composition of the present invention, include, but are not limited to, castor oil, olive oil, peanut oil, sesame oil and the like and mixtures thereof. Preferably, the compositions of the present invention comprise a vegetable oil such as castor oil. The oil may be used in an amount ranging from about 0.005% w/v to about 1.0% w/v. Preferably, the oil is used in an amount ranging from about 0.05% w/v to about 0.5% w/v, most preferably the oil is used in amounts ranging from about 0.1% w/v to about 0.3% w/v. In embodiments where the pharmaceutical composition is a self emulsifying composition, the amount of oil is critical. The amount of oil that may be used in such compositions ranges from 0.1% w/v to 0.3% w/v.

The pharmaceutical composition may additionally comprise other surfactants along with polyethylene glycol hydroxystearate. The term 'emulsifier' and the term 'surfactant' may be used interchangeably. Examples of surfactants that have HLB value more than 10 is used in the pharmaceutical composition. The compositions of the present invention also comprises a surfactant/emulsifier or a mixture of emulsifiers selected from various emulsifiers as described inter alia in standard reference books like "Lachman's—The Theory and Practice of Industrial Pharmacy" $3^{rd}$ edition, pg-513-520, "Remington's Pharmaceutical Sciences", $18^{th}$ edition, pg 298-309, "Handbook of Pharmaceutical Excipients", $3^{rd}$ Edition, pg-see index pg 652 entitled emulsifying agents. The compositions of the present invention may use emulsifier(s) selected from the group consisting of non-ionic, cationic and anionic emulsifier. The emulsifier selected for the invention may be used in an amount ranging from about 0.001% w/v to about 2.0% w/v. Preferably, the emulsifier should be used in an amount ranging from about 0.01% w/v to about 1.0% w/v. More preferably, the emulsifier should be used in an amount ranging from about 0.1% w/v to about 0.5% w/v. Preferably, the compositions of the present invention use emulsifier(s) selected from polysorbates, macrogols, poloxamers, tyloxapol, polyethylene glycol derivatives, polyvinyl alcohol and the like and/or mixtures thereof.

The compositions of the present invention comprises a pharmaceutically acceptable vehicle comprising excipients such as preservatives, osmotic agents/tonicity adjusting agents, buffering agents, pH adjusting agents, viscosity enhancers and other agents that may be used in formulating an ophthalmic composition.

The pharmaceutically acceptable vehicle used in the composition according to the present invention may comprise antimicrobially effective amount of preservative or the composition may be self preserving.

In one embodiment of the present invention, the pharmaceutical composition of the present invention contains preservatives in antimicrobially effective amounts. Antimicrobial effective amounts of a preservative may be determined by performing preservative efficacy tests or antimicrobial effectiveness tests. These tests are inter alia described in chapter 51 of the United States Pharmacopoeia 29-National Formulary 24 (USP 29-NF 24). The preservatives may be used in an amount within the concentration ranges described in standard reference books like 'Remington's Pharmaceutical Sciences' and 'Handbook of Pharmaceutical Excipients'.

The preservative may be selected from the group consisting of acids and their pharmaceutically acceptable salts such as sorbic acid, potassium sorbate, boric acid, borax, salicylic acid, benzoic acid, lactic acid, acetic acid; Aldehydes such as thimerosal; Alcohols such as benzyl alcohol; phenyl ethanol; Phenylmercuric salts such as phenylmercuric acetate and nitrate; Parabens such as methyl and propyl paraben; ethyl paraoxybenzoate or butyl paraoxybenzoate; Halogenated alcohols such as chlorobutanol and the like, and combinations thereof.

Preferably, the compositions of the present invention comprise an antimicrobially effective amount of a preservative comprising a mixture of at least two acid preservatives selected from the group consisting of boric acid, benzoic acid, salicylic acid, sorbic acid, lactic acid and acetic acid or a pharmaceutically acceptable salt thereof. More preferably the pharmaceutical compositions of the present invention comprise a mixture of sorbic acid and/or its pharmaceutically acceptable salt and boric acid and/or its pharmaceutically acceptable salt. These preservatives do not present any irritating effects and have good anti-microbial/anti-septic properties.

The term "sorbic acid" as used herein, applies to both sorbic acid and sorbate salts. Thus, sodium sorbate, potassium sorbate, ammonium sorbate, or any salt of sorbic acid could be used in the methods and compositions disclosed herein and should be interpreted to mean "sorbic acid". It is understood that in an aqueous solution having a pH of 7, sorbic acid, which has a plc of 4.76 will be essentially completely deprotonated. Thus, the actual form of sorbic acid in a composition may be different than that which was added to the composition, and the term "sorbic acid" should be applied as broadly as generally understood in the art in light of these considerations. The sorbic acid or its salt may be used in amounts ranging from about 0.04% w/v to about 2.7% w/v. It is preferred that the sorbic acid or its salt be used in amounts ranging from about 0.07% w/v to about 1.4% w/v. In a preferred embodiment, the preservative used is potassium sorbate in an amount of about 0.47% w/v or sorbic acid in an amount of about 0.35% w/v or about 0.2% w/v.

The term "boric acid" generally refers to boracic acid and includes orthoboric acid and/or metaboric acid and/or tetraboric acid. Salts of boric acid may typically include sodium borate, potassium borate, calcium borate, magnesium borate, manganese borate, and other such borate salts. A preferred salt of boric acid used in the composition of the invention is sodium borate or borax, as it is commonly called. The boric acid or its salt may be used in amounts ranging from about 0.001% w/v to about 4% w/v. It is preferred that the boric acid or its salt be used in amounts ranging from about 0.05% w/v to about 2% w/v. In preferred embodiments of the invention, the boric acid is used along with a pharmaceutically acceptable salt of boric acid. In a preferred embodiment of the invention, the boric acid and the borax are used in amounts ranging from about 0.05% w/v to about 2% w/v each. In a particularly preferred embodiment, the boric acid and the borax are used in amounts of about 0.1% w/v and about 0.11% w/v respectively. In another preferred embodiment, the boric acid and the borax are used in amounts of about 0.3% w/v and about 0.11% w/v respectively. The boric acid and borax mixture in addition to its antimicrobial or preservative properties also functions as a buffer in the composition and is commonly referred to as borate-boric acid buffer. The term "borate-boric acid buffer" generally refers to any combination of boric acid and one or more of the conjugate bases such that the pH is adjusted to the desired range, but preferably it refers to a combination of boric acid and borax. The preservatives that may be used in amounts ranging from about 0.001% w/v to about 4% w/v. It is preferred that the two preservatives be used in amounts ranging from about 0.01% w/v to about 2% w/v.

In addition to the mixture of at least two acid preservatives, the composition of the present invention may optionally contain a chelating agent selected from the group consisting of ethylenediaminetetraacetic acid (EDTA); ethylene glycol-bis-(b-aminoethylether)-N,N,N',N'-tetraacetic acid (EGTA); 1,2-bis(2-aminophenoxy)ethane-N,N,N',N'-tetraacetic acid (BAPTA); ethylene-N,N'-diglycine (EDDA); 2,2'-(ethylendiimino)-dibutyric acid (EDBA); and pharmaceutically acceptable salts thereof. Ethylenediaminetetraacetic acid (EDTA) or its salt, disodium edetate are preferred as chelating agents which may be additionally added to the preservative of the composition of the invention. Ethylenediaminetetraacetic acid (EDTA) or its salt such as disodium edetate may be used in amounts ranging from about 0.009% w/v to about 10% w/v. It is preferred that the EDTA or its salt be used in amounts ranging from about 0.09% w/v to about 2% w/v. In a preferred embodiment, disodium edetate is used as the chelating agent in amounts of about 0.3% w/v of disodium edetate or 0.26% w/v of the EDTA.

The pharmaceutically acceptable vehicle may comprise of osmotic agents. Examples of the osmotic agents that may be used in the compositions of the present invention are selected from the group comprising sodium chloride, potassium chloride, calcium chloride, sodium bicarbonate, sodium carbonate, magnesium sulfate, sodium hydrogen phosphate, sodium dihydrogen phosphate, dipotassium hydrogen phosphate, mannitol, sucrose, glucose and the like, and mixtures thereof. It is known that to be isotonic with the physiological fluids, a fluid has to have an osmolarity of 300 mOsmol/L, but fluids with osmotic pressures ranging from 250 to 375 mOsmol/L are considered isotonic. Fluid with osmolarity less than 250 mOsmol/L are hypotonic whereas those with more than 375 mOsmol/L osmolarity are hypertonic.

The pharmaceutically acceptable vehicle may comprise of buffering agents. Examples of buffering agents that may be used in the pharmaceutical compositions of the present invention may be selected from the group comprising boric acid or salts thereof, phosphoric acid or salts, thereof, citric acid or salts thereof, acetic acid or salts thereof, tartaric acid or salts thereof, trometamol, and the like and mixtures thereof. A particularly preferred buffer of the present invention is the borate-boric acid buffer, which also acts to increase the preservative efficacy of the preservatives added in the composition of the invention. The term "borate-boric acid buffer" generally refers to any combination of boric acid and one or more of the conjugate bases such that the pH is adjusted to the desired range, but preferably it refers to a combination of boric acid and borax.

A pH adjusting agent may be used in order to adjust pH of the compositions of the present invention in the range of about 5.5 to about 7.5. Examples of pH adjusting agents include, but are not limited to hydrochloric acid, citric acid, phosphoric acid, acetic acid, sodium hydroxide, potassium hydroxide, sodium carbonate, sodium hydrogen carbonate and the like, and mixtures thereof.

The pharmaceutically acceptable vehicle may comprise of viscosity enhancers. Viscosity enhancers may be added to the pharmaceutical composition suitable for ophthalmic use to increase the viscosity of the composition and provide a longer residence time in the eye, providing a longer time for drug absorption and effect. The ophthalmic compositions are usually packaged in sterile containers or bottles, which are generally made of plastics. Examples of such viscosity enhancers that may be used in the present invention include hydroxypropylmethylcellulose, hydroxypropylcellulose, polyvinyl alcohol, carboxyvinyl polymers, polyvinylpyrrolidone and the like, and mixtures thereof. In embodiments where the pharmaceutical composition is in the form of emulsion, the viscosity enhancers may be added after the emulsion process.

The pharmaceutical composition of the present invention may or may not comprise of a co-solvent. It may be noted that the microemulsion is formed without the need of a co-solvent. In certain embodiments, a co-solvent may be used to enhance the surfactant effect. Examples of the co-solvents that may be used include but are not limited to propylene glycol, polyethylene glycol, glycerine and the like and mixtures thereof. The co-solvent used is present in an amount of at least about 1.2% w/v. The propylene glycol may be used in amounts ranging from about 1.2% w/v to about 3% w/v, or preferably from about 1.5% w/v to about 2.5% w/v, more preferably from about 1.5% w/v to about 2% w/v and most preferably in an amount of about 1.5% w/v.

The pharmaceutical composition of the present invention is sterile. Sterility is best achieved through sterile filtration using a sterile membrane filter of 0.45 or 0.2 microns pore size and filtering into a sterile container. Other methods of sterilization known in the art such as dry heat, steam under pressure and gas sterilization can also be used to make the pharmaceutical compositions for ophthalmic use sterile. Ophthalmic compositions are generally packaged in multiple use containers. Since there is a possibility of inadvertent bacterial contamination of the formulation with repeated patient use, a preservative is generally added. Preservatives that do not cause patient sensitivity or that are compatible with the other ingredients in the formulation are generally used.

In one embodiment of the present invention, the pharmaceutical composition comprises latanoprost, polyethylene glycol hydroxystearate and castor oil. The amount of the surfactant and the oil may be adjusted to get a submicron emulsion with an average droplet size less than 100 nm and a percent transmission greater than 70%. In a preferred embodiment, the amount of castor oil varies from about 0.15% to about 0.3% and the amount of polyethylene glycol hydroxystearate varies from about 0.25% to about 0.5% weight by volume of the composition. The composition according to this embodiment is free of any quaternary ammonium compounds such as benzalkonium chloride which acts as a preservative. It was found that such composition was self emulsifying. It is always advantageous to have a self emulsifying system compared to the conventional emulsions where an external energy supply is necessary for emulsification. It may be important to note that a proper selection of oil, surfactant and optionally a co-solvent based on the solubility of the drug, leads to an effective self emulsifying pharmaceutical composition.

In one embodiment of the present invention, where an oil is incorporated, the composition was found to have a zeta potential in a range from about −0.1 mV to about −60 mV and the droplet size of the oil dispersed in aqueous medium was not more than 100 nm. Preferred compositions have zeta potential value of less than −20 mV. When such composition was stored in natural low density polyethylene containers, the said composition was found to show no sorption problem when stored at room temperature.

According to one embodiment, the pharmaceutical composition is prepared by first dissolving the active ingredient completely in the oil by stirring. The emulsifier is melted and added to the oily phase and mixed properly. Further, this phase is added drop wise under continuous stirring to an aqueous phase, comprising water for injection heated at 55-60° C. This leads to the formation of an almost transparent micro-emulsion or swollen micelles. To this propylene glycol is added at approximately the same temperature. Further, the temperature is lowered to 25-30° C. and along with stirring the above emulsion phase is added to a pre-formed solution of buffer, preservatives and other salts in water for injection and having a pH of about 6.5-7.5. Finally, the pH is adjusted to 7.00 using HCl or NaOH; the volume made-up to 100% using water for injection and the composition is filtered aseptically using 0.2 μm membrane filter.

In another embodiment, the pharmaceutical composition comprises prostaglandin derivatives, stabilizing amount of polyethylene glycol hydroxystearate and pharmaceutically acceptable vehicle. The pharmaceutical composition is prepared by first heating the polyethylene glycol hydroxystearate (Solutol HS 15) in a separate glass beaker at 65°-70° C. until it melts. To this, the drug and other ingredients i.e preservatives, buffers were added. The composition is diluted with water for injection and the pH was adjusted with sodium hydroxide and hydrochloric acid.

The pharmaceutical compositions of the present invention were tested for efficacy in reduction of intraocular pressure (IOP) in glaucomatous rabbits and normotensive dogs. It was observed that the compositions of the present invention significantly reduced the IOP in both glaucomatous rabbits and normotensive dogs as well as it had a significant effect (miosis) on the pupillary diameter.

According to one embodiment of the present invention the pharmaceutical composition comprises oil along with polyethylene glycol hydroxystearate. In this embodiment, it was surprisingly found that pharmaceutical compositions showed same therapeutic activity compared to the composition that does not contain any oil, for example, Xalatan®. Without wishing to be bound by any theory, the applicants believe that this was surprising because generally the oil is known to hinder the diffusion of the drug and thereby affect the ocular availability.

The pharmaceutical compositions of the present invention were tested in New Zealand White Rabbits, for ocular irritancy potential and systemic toxicity. The pharmaceutical composition of the present invention and polyethylene glycol hydroxystearate (the excipient) both were tested. The test involved daily repeated ocular instillation for at least 14 days. It was observed that on dosing of polyethylene glycol hydroxystearate (Solutol HS 15) at approximately 47 times the human recommended dose (HRD) and latanoprost present in the pharmaceutical composition at approximately 48 times the HRD, no clinical sign or irritation in the eyes was observed. There were no statistically significant alterations in body weight, % body weight gain, terminal body weight, absolute and relative organ weights, differential cell count of bone marrow, biochemical and hematological parameters after administration of polyethylene glycol hydroxystearate and latanoprost, as compared to the control group. Also the treatment with polyethylene glycol hydroxystearate and latanoprost did not result into any gross or microscopical pathological lesion. Thus, it was found that the pharmaceutical composition of the present invention was safe and did not produce any toxic reactions, ocular irritancy or systemic toxicity.

The following examples illustrate the scope of the present invention without any limitation thereto.

EXAMPLE 1-2

The pharmaceutical composition of the present invention was prepared as described in Table 1 below.

TABLE 1

Composition according to example 1 and example 2

| Ingredients | Example 1 | Example 2 |
|---|---|---|
| | Quantity % w/v | |
| Latanoprost | 0.005 | |
| Propylene glycol | 1.5 | |
| Polyethyleneglycol 15 Hydroxy-stearate (Solutol HS 15) | 0.25 | |
| Castor oil | 0.15 | |
| Potassium sorbate | 0.47 | |
| Borax | 0.11 | |
| Boric acid | 0.10 | 0.30 |
| Sodium Edetate | — | 0.30 |
| Sodium Hydroxide | qs | |
| Hydrochloric acid | qs | |
| Water for Injection (WFI) | qs | |

Latanoprost and castor oil was taken in a glass beaker and the mixture was stirred continuously using a dry glass rod, untill complete solubilization of latanoprost takes place. Polyethyleneglycol 15 Hydroxystearate (Solutol HS 15) was heated in a separate glass beaker at 65°-70° C. until it melts. After melting, it was transferred to the above oil phase and stirred using dry glass rod at 65-70° C. On complete mixing, the oil phase solution temperature was allowed to come down to 60° C. with gentle stirring. The temperature of the oil phase was maintained at around 55-60° C. This oil phase was added drop wise under continuous stirring to an aqueous phase comprising water for injection heated at 55-60° C. This leads to the formation of transparent micro-emulsion. This is followed by addition of propylene glycol at 55-60° C. The temperature was allowed to come down to 25°-30° C. with gentle stirring, the stirring being continued for another 30-45 minutes at 25°-30° C. This was then added to a preformed solution of potassium sorbate, borax and boric acid in water for injection and having a pH of about 6.5-7.5. Finally, the pH was checked and if required, was adjusted to 7.00 by adding HCl or NaOH solution. The volume was made up to 100% by rinsing the manufacturing vessels with WFI and the composition was aseptically filtered through 0.2 µm membrane filter. The composition was filled into naturally occurring low density polyethylene containers.

The composition was stored at accelerated stability conditions i.e 25° C./60% RH or 40° C./75% RH. The stability studies results are given in Table 2.

TABLE 2

Accelerated stability studies of the composition of example 1 stored in LDPE containers

| Storage Conditions | Latanoprost Assay (Limit: 90.0-110.0% of Label Claim) | |
|---|---|---|
| | Example 1 | Example 2 |
| Initial | 109.11 | 103.59 |
| Fridge (2-8° C.) | | |
| 1 Month | 109.70 | 103.88 |
| 3 Month | 107.67 | 102.48 |
| 6 month | — | 101.00 |
| 25° C./60% RH | | |
| 1 Month | 108.11 | 103.16 |
| 3 Month | 106.39 | 101.60 |
| 6 month | — | 99.71 |

TABLE 2-continued

Accelerated stability studies of the composition of example 1 stored in LDPE containers

| Storage Conditions | Latanoprost Assay (Limit: 90.0-110.0% of Label Claim) | |
|---|---|---|
| | Example 1 | Example 2 |
| 40° C./75% RH | | |
| 1 Month | 106.94 | 100.77 |
| 3 Month | 103.83 | 95.38 |
| 6 month | — | 93.50 |

The results indicate that the pharmaceutical composition of the present invention is stable at room temperature, without any significant sorption of the drug to the LDPE containers. The data indicates that the assay of latanoprost remained unchanged upon storage at accelerated condition. This indicates that the micro-emulsion prepared according to the present invention solved the sorption problem. The pharmaceutical composition showed an average droplet size of about 100 nm; percent transmittance was more than 80%, and zeta potential of −10 mV.

EXAMPLE 3-5

The pharmaceutical compositions of the present invention were prepared as described in Table 3 below.

TABLE 3

| Ingredients | Example 3 | Example 4 | Example 5 |
|---|---|---|---|
| | Quantity % w/v | | |
| Latanoprost | 0.005 | 0.005 | 0.005 |
| Polyethylene Glycol | — | 1 | 1 |
| Polyethyleneglycol 15 Hydroxystearate (Solutol HS 15) | 0.25 | 0.25 | 0.25 |
| Castor oil | 0.15 | 0.15 | 0.15 |
| Potassium sorbate | 0.47 | — | — |
| Zinc chloride | — | 0.0025 | 0.0025 |
| Borax | 0.1 | — | — |
| Boric acid | 0.30 | 0.50 | 0.50 |
| Disodium Edetate | 0.30 | — | 0.30 |
| Trometamine | — | q.s | q.s |
| Sodium Hydroxide | qs | — | — |
| Hydrochloric acid | qs | — | — |
| Water for Injection (WFI) | qs | q.s | q.s |

Compositions according to Examples 3, 4 and 5 were prepared by process similar to the one described for Example 1 and 2. The droplet size, the zeta potential and percent transmittance values were comparable to the composition of Example 1 and 2.

EXAMPLE 6

The pharmaceutical composition of the present invention was prepared as described in Table 4 below.

TABLE 4

| Ingredients | Quantity % w/v |
|---|---|
| Latanoprost | 0.005 |
| Borax | 0.11 |
| Boric acid | 0.10 |

TABLE 4-continued

| Ingredients | Quantity % w/v |
|---|---|
| Propylene glycol | 1.5 |
| Potassium sorbate | 0.47 |
| Polyethyleneglycol 15 Hydroxystearate (Solutol HS 15) | 0.25 |
| Sodium hydroxide | q.s |
| Hydrochloric acid | q.s |
| Water for injection (WFI) | q.s |

Solutol HS 15 was taken in a glass beaker and heated at 65° to 70° C. until melted. After melting, it was transferred to the beaker containing latanoprost & stirred till complete mixing. This phase was added to water for injection heated at 65°-70° C. drop wise with mild stirring followed by adding propylene glycol at 55°-60° C. under stirring. In another beaker potassium sorbate, disodium edetate, borax and boric acid were dissolved in water for injection (WFI) under mild stirring. This solution was added to the above microemulsion phase at the temperature of 20°-25° C. under stirring. The pH was adjusted to 7.00 by adding HCl or NaOH solution. The volume was made up to 100% by rinsing the manufacturing vessel with WFI and filtered through 0.2 µm membrane filter. The composition thus prepared was stored in low density polyethylene containers and was subjected to accelerated stability study. The stability study results are tabulated in table 5.

TABLE 5

Accelerated stability studies of the composition of example 6 stored in LDPE containers

| Storage condition | Latanoprost Assay (Limit: 90.0-110.0% of Label Claim) | pH |
|---|---|---|
| Initial | 105.11 | 7.23 |
| Fridge (2-8° C.) | | |
| 1 M (Up) | 105.28 | 7.15 |
| 25° C./60% RH | | |
| 1 M (Up) | 103.43 | 7.09 |
| 1 M (Inverted) | 103.26 | 7.06 |
| 30° C./65% RH | | |
| 1 M (Up) | 102.02 | 6.68 |
| 1 M (Inverted) | 102.35 | 6.99 |
| 40° C./75% RH | | |
| 1 M (Up) | 94.88 | 7.14 |
| 1 M (Inverted) | 92.45 | 7.15 |

It was observed that when the solution of example 6 was stored at room temperature or at 25° C./60% RH, there was no sorption problem observed. In view of the stability results, it may be advisable to store the solution of example 6 at Fridge (2° C.-8° C.) or it may stored in suitable containers such as coated containers.

EXAMPLE 7

The pharmaceutical composition of the present invention containing bimatoprost as the prostaglandin is given in Table 6 below.

TABLE 6

| Ingredients | Quantity % w/v |
|---|---|
| Bimatoprost | 0.03 |
| Propylene glycol | 1.5 |
| Polyethyleneglycol 15 Hydroxystearate (Solutol HS 15) | 0.3 |
| Castor oil | 0.15 |
| Potassium sorbate | 0.47 |
| Borax | 0.11 |
| Boric acid | 0.3 |
| Disodium EDTA | 0.3 |
| Sodium Hydroxide | qs |
| Hydrochloric acid | qs |
| Water for Injection (WFI) | qs |

The composition of bimatoprost prepared according to this example was characterized by determining the average droplet size of the oil globules, the percent transmittance and the zeta potential. The micro emulsion showed an average droplet size of 67.6 nm; percent transmittance of 90.2%, and zeta potential of −5.21 mV.

EXAMPLE 8

Comparative Example

TABLE 7

| Ingredients | Quantity % w/v |
|---|---|
| Latanoprost | 0.005 |
| Borax | 0.11 |
| Boric acid | 0.10 |
| Propylene glycol | 1.5 |
| Potassium sorbate | 0.47 |
| Sodium hydroxide | q.s |
| Hydrochloric acid | q.s |
| Water for injection (WFI) | q.s |

The above composition was prepared by simple mixing of the mentioned ingredients. When the composition was stored in LDPE containers, there was unacceptable reduction in the latanoprost assay (see table 8 below) indicating an unacceptable sorption of latanoprost to the containers.

TABLE 8

Accelerated stability studies of the composition of example 8 stored in LDPE containers

| Storage condition | Latanoprost Assay (Limit: 90.0-110.0% of Label Claim) | pH |
|---|---|---|
| Initial | 97.82 | 7.15 |
| Fridge (2-8° C.) | | |
| 1 M | 91.50 | 7.24 |
| 2 M | 88.55 | 7.20 |
| 3 M | 79.38 | 7.24 |
| 25° C./60% RH | | |
| 1 M (Up) | 85.74 | 7.11 |
| 1 M (Inverted) | 85.68 | 7.01 |
| 2 M (Up) | 79.38 | 7.11 |

EXAMPLE 9

Comparative Example

TABLE 9 composition of comparative example

| Ingredients | Quantity % w/v |
|---|---|
| Latanoprost | 0.005 |
| Propylene glycol | 1.5 |
| Polysorbate 80 | 0.25 |
| Castor oil | 0.15 |
| Potassium sorbate | 0.47 |
| Borax | 0.11 |
| Boric acid | 0.3 |
| Disodium Edetate | 0.3 |
| Sodium Hydroxide | qs |
| Hydrochloric acid | qs |
| Water for Injection (WFI) | qs |

The composition prepared according to this example showed an average droplet size of 173 nm; percent transmittance 35.0%, and zeta potential of −8.36 mV.

We claim:

1. A pharmaceutical composition suitable for ophthalmic use comprising 0.005% w/v latanoprost or a pharmaceutically acceptable salt therof, 0.15% w/v castor oil, 0.2 to 0.75% w/v of polyethylene glycol hydroxystearate, a co-solvent, a chelating agent, a preservative, and pharmaceutically acceptable vehicle,
   wherein the ratio of oil to polyethylene glycol hydroxystearate is less than 1.0,
   wherein the composition is in the form of a self-emulsifying micro-emulsion with average droplet size of about 100 nm or less and a zeta potential between −0.1 mV to −20 mV,
   wherein the composition does not comprise a cationic surfactant, and
   wherein the composition does not comprise a quaternary ammonium compound.

2. The pharmaceutical composition as claimed in claim 1 Wherein the emulsion has an average droplet size of less than 100 nanometers in diameter.

3. The pharmaceutical composition as claimed in claim 2, wherein the emulsion has a percent transmission greater than 70%.

4. The pharmaceutical composition as claimed in claim 2, wherein the emulsion has a percent transmission greater than 80%.

5. The pharmaceutical composition as claimed in claim 1 wherein the composition does not show any clinical sign of ocular irritation when tested in rabbits.

* * * * *